United States Patent [19]

Endo et al.

[11] Patent Number: 5,242,815
[45] Date of Patent: Sep. 7, 1993

[54] PROCESS FOR PREPARATION OF STREPTOVARICIN

[75] Inventors: Isao Endo, Kokubunji; Shigehiro Nagura, Joetsu; Kaname Inoue, Kawasaki; Jun Watanabe, Tanashi, all of Japan

[73] Assignees: Shin-Etsu Chemical Co., Ltd., Tokyo; The Institute of Physical Chemical Research, Saitama, both of Japan

[21] Appl. No.: 875,369

[22] Filed: Apr. 29, 1992

Related U.S. Application Data

[62] Division of Ser. No. 601,875, Oct. 23, 1990, Pat. No. 5,126,254.

[30] Foreign Application Priority Data

Jan. 24, 1990 [JP] Japan .................................. 2-14285
Jan. 24, 1990 [JP] Japan .................................. 2-14286

[51] Int. Cl.$^5$ .................. C12P 17/18; C12P 17/08; C12P 19/62; C12R 1/465
[52] U.S. Cl. .................................. 435/119; 435/121; 435/124; 435/245; 435/253.6; 435/886
[58] Field of Search .................... 435/119, 253.5, 245, 435/121, 124, 886, 253.6

[56] References Cited

U.S. PATENT DOCUMENTS

| 4,277,564 | 7/1981 | Johnson | 435/242 |
| 4,521,516 | 6/1985 | Lemme et al. | 435/245 |
| 4,713,241 | 12/1987 | Wakisaka et al. | 435/71.3 |
| 5,114,846 | 5/1992 | Inoue et al. | 435/119 |
| 5,126,254 | 6/1992 | Endo et al. | 435/119 |
| 5,137,825 | 8/1992 | Inoue et al. | 435/886 |
| 5,177,018 | 1/1993 | Inoue et al. | 435/245 |

OTHER PUBLICATIONS

K. L. Rinehart Jr., et al. "Relative Biological Activities of Individual Streptovaricins & Acetates", Biochem. vol. 13, No. 5, pp. 861-867 (1974).
K. Sasaki et al. "Chemical Modification of Streptovaricins C", J. Antibiotics vol. 29, No. 2, pp. 147-154 (Feb. 1976).

Primary Examiner—Herbert J. Lilling
Attorney, Agent, or Firm—McAulay Fisher Nissen Goldberg & Kiel

[57] ABSTRACT

A method for producing streptovaricin by culturing a streptovaricin producing strain in the presence of a nonionic adsorbent. This procedure substantially increases the production efficiency of the streptovaricin. A second embodiment wherein the streptovaricin producing strain is produced in the presence of fumaric acid or its water soluble salts to provide improvements in production efficiency is also disclosed.

6 Claims, No Drawings

PROCESS FOR PREPARATION OF STREPTOVARICIN

This is a division of application Ser. No. 07/601,875, filed Oct. 23, 1990, now U.S. Pat. No. 5,126,254.

BACKGROUND OF THE INVENTION

I. Field of the invention

This invention concerns a process for the preparation of streptovaricin having a high production efficiency.

II. Description of the Prior Art

Five types of streptovaricins are known, designated as A, B, C, D, and E, (U.S. Pat. No. 3,116,202). Initially, they drew attention because of their usefulness as an antituberculosis antibiotic. Recently, it has been found that derivatives obtained by chemically modifying streptovaricins, and particularly, Streptovaricin C, are useful as anti-retroviral agents, anti-cancer agents or the like. See Japanese published pre-examination patent application No. 110,000/1979.

A known process for the preparation of streptovaricins comprises fermenting a submerged culture of *Streptomyces spectabilis*, U.S. Pat. No. 3,116,202. However, this preparation process has a low productive efficiency and only a very small amount of streptovaricin was obtained. The apparent reason is that the produced streptovaricin is rapidly decomposed in the medium. Moreover, because the streptovaricin produced has a high lipid solubility, it accumulates on the surface of the hyphae which suppresses production. Therefore, this process is difficult to use industrially. A method has been disclosed wherein a nonionic resin has been added to the fermentation both for clycloheimide fermentation. However, this resulted in only a two to three fold improvement in production efficiency. See H. Wang, Annuals New York Academy of Sciences, 431, 1483, pp. 313–321.

SUMMARY OF THE INVENTION

We have discovered a process capable of preparing streptovaricin in a high productive efficiency. More particularly, we have discovered a process for avoiding accumulation of the streptovaricin at the hyphae surface and the concomitant suppression of streptovaricin product. In one embodiment, the inventive process comprises culturing a streptovaricin-producing strain belonging to the genus Streptomyces in the presence of a nonionic adsorbent. In a second embodiment, the inventive process comprises culturing a streptovaricin-producing strain belonging to the genus Streptomyces in the presence of at least one member selected from the group consisting of fumaric acid and its water soluble salts. In yet a third embodiment, the inventive process comprises culturing a streptovaricin-producing strain belonging to the genus Streptomyces in the presence of a nonionic adsorbent and at least one member selected from the group consisting of fumaric acid and its water soluble salts.

DESCRIPTION OF THE PREFERRED EMBODIMENT

In the practice of the process of the present invention, the nonionic adsorbent can be added to the fermentation medium before or after the start of fermentation, but it is preferred that the adsorbent be added before the medium is inoculated with the bacterium.

The amount of anionic resin and/or water-soluble fumarate or fumarate salt which is that amount which is effective to increase the streptovaricin production.

The streptovaricin-producing strain belonging to the genus Streptomyces usable in the process of the present invention includes, for example, *Streptomyces spectabilis* ATCC 27465. With the inventive process, the streptovaricins produced move promptly to the nonionic adsorbent and are absorbed thereto. Consequently, the streptovaricins are not easily decomposed in the medium, and do not accumulate on the surface of the hyphae. In turn, suppression of the activity of the bacterium is minimized and production of streptovaricins is effectively sustained.

The amount of adsorbent added to the medium is preferably in the range of from about 0.1 to about 20%, and preferably about 0.5 to about 10% by weight.

Suitable for use as nonionic adsorbents are porous fine particles having a large specific surface area and consisting of various synthetic resins, such as, polymers of one or more compounds selected from the group consisting of styrene, divinylbenzene, and acrylic esters. Specific examples include adsorbents composed of styrene-divinylbenzene type synthetic resins, for example, HP-10, HP-20, HP-30, HP-40, and HP-50, produced by MITSUBISHI KASEI CORPORATION; Amberlite XAD-2 and XAD-4, produced by Rohm and Haas Co.; adsorbents composed of acrylic ester type resins, for example, Amberlite XAD-7, produced by Rohm and Haas Co.; and the like. Particularly preferred among these nonionic adsorbents are those having a particle size of from about 50 to about 1,000 $\mu$m, a specific surface area of from about 50 to about 1,000 m$^2$/g and a pore volume of from about 0.2 to about 1.5 g/ml.

In another embodiment of this invention, at least one member selected from the group consisting of fumaric acid and its water soluble salts may be added to the medium. This addition enhances production of the streptovaricins, and particularly Streptovaricin C.

Suitable water soluble salts include potassium fumarate, sodium fumarate, potassium sodium fumarate, monopotassium fumarate, monosodium fumarate, and the like. Fumaric acid and the above exemplified fumarates can be used alone or in any combination with one another.

In yet another embodiment, both the nonionic adsorbent and fumaric acid or water soluble salt thereof may be added to the medium.

Preferably, the amount of fumaric acid or its water soluble salt added to the medium is from about 0.1 to about 10%, and particularly from about 0.5 to about 5% by weight in terms of fumaric acid based on the medium. The fumaric acid or its salt can be added to the medium either before or after the start of fermentation, but it is preferred that it is added before.

Conditions conventionally adopted for the preparation of antibiotics by culturing of microorganisms can be used. Generally, the microorganisms are cultured in an aqueous medium containing a nitrogen source, an assimilable carbon source, and an inorganic salt, under aerobic conditions.

As a nitrogen source, any of the known inorganic and organic nitrogen sources can be used. Examples include organic nitrogen sources, such as, beef extract, peptone, vegetable proteins (e.g., soybean meal), casein, malt extract, fish meal, cotton meal, keisoy (defatted soybean fine powder), peanut meal, yeast for brewing, corn gluten meal and corn steep liquor; and inorganic nitrogen sources, such as, ammonium sulfate, ammonium nitrate, and potassium nitrate.

Assimilable carbon sources include, for example, glucose, dextrin, molasses, starch, maltose, galactose, mannitol, sucrose, lactose, soybean oil, and the like.

Nutritious inorganic salts include, for example, salts which form ions, such as, sodium, calcium, phosphate, and sulfate, and specific examples thereof include calcium carbonate, potassium phosphate, magnesium sulfate, potassium chloride, sodium chloride, zinc sulfate, ferrous sulfate, manganese sulfate, cobalt chloride, ammonium molybdate, and the like.

During culturing, the pH of the medium is in the range from about 5.5 to about 7.5, and the temperature is in the range from about 23° C. to 37° C., preferably from about 25° C. to 30° C. The maximum yield can be obtained by culturing for a period of from about 4 to 8 days.

With the embodiment of the present invention wherein the streptovaricins obtained are adsorbed on the nonionic adsorbent, it is necessary to separate the streptovaricins from the nonionic adsorbent after separation of the nonionic adsorbent from the medium.

The separation of the adsorbent can be achieved by filtering the medium or utilizing the difference in specific gravity between the nonionic adsorbent and the medium, e.g., decantation, centrifugation, and the like.

The streptovaricins may be separated from the nonionic adsorbent by washing the separated adsorbent with a suitable organic solvent or a mixed solvent of an organic solvent and water to elute the adsorbed streptovaricin. Examples of suitable organic solvents include methanol, ethanol, acetone, acetonitrile, ethyl acetate, dichloroethane, chloroform, and the like, and any mixture thereof. Also mixed solvents of one or more of these organic solvents with water may be used. In order to effectively elute streptovaricins, it is preferred that the adsorbent on which the streptovaricins are adsorbed be washed first with an aqueous solution having a low organic solvent concentration, preferably less than 25%, followed by a wash with an aqueous solution having a high organic solvent concentration, preferably more than 40%.

Since Streptovaricin C is the most useful of the streptovaricins obtained, it is desirable that during the separation from the adsorbent, Streptovaricin C can be selectively separated. Preferred for this purpose is an acetonitrile-water mixed solvent. Streptovaricin C can be selectively separated when the adsorbent containing streptovaricins is washed first with low acetonitrile/water mixture (preferably less than 25% acetonitrile, and most preferably from 10 to 20% acetonitrile), and then is eluted with high acetonitrile/water mixture (preferably more than 40%, and most preferably from 40 to 60% acetonitrile).

The thus obtained streptovaricins can be further purified, for example, by repeated recrystallization, silica gel column chromatography, and the like.

EXAMPLES

The following examples illustrate the present invention.

EXAMPLE 1

A culture of *Streptomyces spectabilis* ATCC 27465 strain was inoculated into a seed medium in a 500 ml flask. The seed medium was prepared by mixing 1.25 g of N-Z amine A (hydrolyzed casein); 0.63 g of glucose; 0.63 g of enzyme-decomposed extract of soybean (Soytone); 0.16 g of monopotassium phosphate; 0.16 g of dipotassium phosphate; and 100 ml of distilled water. The flask was placed on a rotary shaker and cultured at a temperature of 27° C. with agitation by rotating at 200 rpm for 72 hours to obtain a seed culture.

A preproduction culture was then prepared by inoculating 2 ml of the seed culture into a preproduction medium in a 500 ml flask composed of 1 g of defatted soybean powder (Kay Soy), 1 g of corn steep liquor, 2 g of corn starch, 0.25 g of beer yeast, 0.3 g of potassium chloride, 0.4 of calcium carbonate, and 100 ml of distilled water. The flask was then set up on a rotary shaker and was cultured at a temperature of 27° C. with agitation by rotating at 200 rpm for 48 hours to produce the preproduction culture.

A previously prepared production medium was inoculated with 5 ml of the preproduction culture in a 500 ml flask. The production medium was prepared by mixing 4 g of soybean meal, 4 g of glucose, 0.25 g of beer yeast, 0.3 g of sodium chloride, 0.05 g of calcium carbonate, 0.25 g of magnesium sulfate, 0.25 g of potassium monohydrogen phosphate, 3 g of a polystyrene adsorbent (trade name: Diaion HP-20), and 100 ml of distilled water. The flask was set up on a rotary shaker, and culturing was carried out at 28° C. for 6 days. Thereafter, the culture broth was filtered using a net to separate the adsorbent from the medium. The separated adsorbent was washed with a mixed solvent of ethyl alcohol-ethyl acetate (1:1), to elute the adsorbed substances. After washing, the solvent was analyzed by high performance liquid chromatography (HPLC), which indicated the presence of 0.4 mg of Streptovaricin C.

COMPARATIVE EXAMPLE 1

The same culturing method as in Example 1 was used except that the production medium did not contain the polystyrene type adsorbent. HPLC showed the production of 0.05 mg of Streptovaricin C.

EXAMPLE 2

The same culturing method as in Example i was used, except that the production also contained monosodium fumarate. The medium was prepared by mixing 4 g of soybean meal, 4 g of glucose, 0.25 g of beer yeast, 0.3 g of sodium chloride, 0.05 g calcium carbonate, 0.25 g of magnesium sulfate, 0.25 g of potassium monohydrogen phosphate, 1.2 g of monosodium fumarate, 3 g of polystyrene type adsorbent (trade name: Diaion HP 20), and 100 ml of distilled water. HPLC analysis showed that 3.6 mg of Streptovaricin C was produced.

COMPARATIVE EXAMPLE 2

The same method of culturing as in Example 2 was used except the production medium did not contain the polystyrene type adsorbent. 0.08 mg of Streptovaricin C was obtained.

EXAMPLE 3

The amount of Streptovaricin C in the adsorbed substances in Example 2 was 10% by weight according to HPLC analysis at 254 nm of the adsorbent after separation from the medium. The adsorbent was washed with an aqueous 15% acetonitrile solution, then eluted with an aqueous 50% acetonitrile solution and evaporated to dryness. The solid crude product obtained contained 50% by weight of Streptovaricin C.

The inventive process thus provides at least a ten-fold to twenty-fold or greater increase in efficiency of streptovaricin production as compared to the results obtained with comparative example 1.

EXAMPLE 4

A culture of *Streptomyces spectabilis* ATCC 27465 strain was inoculated into a seed medium in a 500 ml flask. The seed medium was prepared by mixing 1.25 g of N-Z amine A; 0.63 g of glucose; 0.63 g of enzyme-decomposed extract of soybean, 0.16 g of monopotassium phosphate; 0.16 g of dipotassium phosphate, and 100 ml of distilled water. The flask was placed on a rotary shaker and cultured at a temperature of 27° C. with agitation by rotating at 200 rpm for 72 hours to obtain the seed culture.

A preproduction culture was then prepared by inoculating 2 ml of the seed culture into a preproduction medium in a 500 ml flask composed of 1 g of defatted soybean powder; 1 g of corn steep liquor; 2 g of corn starch; 0.25 g of beer yeast; 0.3 g of potassium chloride; 0.4 of calcium carbonate; and 100 ml of distilled water. The flask was then set up on a rotary shaker and was cultured at a temperature of 27° C with agitation by rotating at 200 rpm for 48 hours to produce the preproduction culture.

Then, 100 milliliters of the preproduction culture that had been obtained in the manner described above were introduced into a production medium prepared by mixing 80 g of soy beans, 80 g of glucose, 5 g of beer yeast, 6 g of sodium chloride, I g of calcium carbonate, 24 g of monosodium fumarate and 2 liters of distilled water, in a five-liter jarfermenter.

The inoculated production medium was cultured by stirring at 500 rpm while air was introduced at a rate of five v/v per minute at a temperature of 27° C. The amount of streptovaricin accumulated in the fermentation medium reached its maximum after the passage of 70 hours.

At this time, the concentration of Streptovaricin C in the production medium was 7.6 mg per liter and the amount of the bacteria was 24.5 g/1 (as dry bacteria).

COMPARATIVE EXAMPLE 4

Culturing was carried out in the same manner as described in Example 4 except that the fermentation medium did not contain any monosodium fumarate. The amount of streptovaricin accumulated reached its maximum after 90 hours. At this time, the concentration of Streptovaricin C was 2.4 mg/1 and the amount of the bacteria was 29 g/1 (as dry bacteria).

What is claimed is:

1. In a process for the preparation of streptovaricin wherein a streptovaricin-producing strain belonging to the genus Streptomyces is cultured in a medium containing a nitrogen source, an assimilable carbon source and an inorganic salt, the improvement which comprises carrying out the culturing step in a medium containing at least one member selected from the group consisting of fumaric acid and its water soluble salts.

2. The process of claim 1 wherein said water soluble salt is selected from the group consisting of potassium fumarate, sodium fumarate, potassium sodium fumarate, monopotassium fumarate, monosodium fumarate, and combinations thereof.

3. The process of claim 1 wherein said medium is cultured at a pH of from about 5.5 to 7.5.

4. The process of claim 1 wherein said medium is cultured at a temperature of from about 23° C. to 37° C.

5. The process of claim 1 wherein said medium is cultured at a temperature of from about 25° C. to 30° C.

6. The process of claim 1 wherein said medium is cultured for about 4 to 8 days.

* * * * *